United States Patent [19]
Teicher et al.

[11] Patent Number: 5,676,978
[45] Date of Patent: Oct. 14, 1997

[54] METHODS OF INHIBITING UNDESIRABLE CELL GROWTH USING A COMBINATION OF A CYCLOCREATINE COMPOUND AND A HYPERPLASTIC INHIBITORY AGENT

[75] Inventors: Beverly A. Teicher, Needham; Donald W. Kufe, Wellesley; Rima Kaddurah-Daouk, Belmont, all of Mass.

[73] Assignees: Amira, Inc., Cambridge; Dana-Farber Cancer Institute, Boston, both of Mass.

[21] Appl. No.: 185,438

[22] Filed: Jan. 21, 1994

Related U.S. Application Data

[63] Continuation-in-part of Ser. No. 610,418, Nov. 7, 1990, Pat. No. 5,324,731, which is a continuation-in-part of Ser. No. 467,147, Jan. 18, 1990, abandoned, which is a continuation-in-part of Ser. No. 344,963, Apr. 28, 1989, abandoned, which is a continuation-in-part of Ser. No. 310,773, Feb. 14, 1989, abandoned.

[51] Int. Cl.$^6$ .............. A61K 33/24; A61K 31/35; A61K 31/415; A61K 31/65
[52] U.S. Cl. .............. 424/649; 514/90; 514/392
[58] Field of Search .............. 424/649; 514/392, 514/398, 428, 210, 90, 274, 456, 460, 563, 565

[56] References Cited

U.S. PATENT DOCUMENTS

| | | | |
|---|---|---|---|
| 4,766,149 | 8/1988 | Osswald et al. | 514/553 |
| 5,321,030 | 6/1994 | Kaddurah-Daouk et al. | 514/275 |
| 5,324,731 | 6/1994 | Kaddurah-Daouk et al. | 514/275 |

FOREIGN PATENT DOCUMENTS

| | | |
|---|---|---|
| 0 007 597 | 2/1980 | European Pat. Off. |
| WO 9208456 | 5/1992 | WIPO . |
| WO 9416687 | 8/1994 | WIPO . |
| WO 9416712 | 8/1995 | WIPO . |

OTHER PUBLICATIONS

Bergmann et al. . "Synthese des Kreatines aus Sarkosin und Arginin—Neue Synthese des Methylguanidins", *Z. Physiol. Chem.* 173, 80–83 (1928).

Rowley et al. "On the Specificity of Creatine Kinase, New Glycocyamines and Glycocyamine Analogs Related to Creatine", *J. Am. Chem.*, 247:5542–5551 (Oct. 1971).

McLaughlin et al., "Specificity of Creatine Kinase for Guanidino Substrates", *J. Biol. Chem.*, 247:4382–4388 (Jul. 1972).

(List continued on next page.)

*Primary Examiner*—S. Mark Clardy
*Attorney, Agent, or Firm*—Elizabeth A. Hanley; Lahive & Cockfield, LLP

[57] ABSTRACT

The present invention provides for the use of creatine compounds and hyperplastic inhibitory agents for prophylactic and/or therapeutic treatments of undesirable cell growth, e.g. tumors. The present invention provides methods of using creatine compounds, in combination with a hyperplastic inhibitory agent, to inhibit the growth of undesirable cells in a subject. The present invention is based, at least in part, on the discovery that creatine compounds and hyperplastic inhibitory agents, such as inhibitory agents, additively and synergistically combine to inhibit cell growth. The present invention further pertains to compositions for inhibiting undesirable cell growth in a subject. The compositions of the present invention include an effective amount of the creatine compound and a hyperplastic inhibitory agent in a pharmaceutically acceptable carrier. Other aspects of the invention include packaged creatine compounds and inhibitory agents. The packaged compounds and agents also include instructions for using the creatine compound/inhibitory agent combination for inhibiting undesirable cell growth in a patient or instructions for using the compounds and agents, in selected quantities, in a pharmaceutically acceptable carrier.

65 Claims, 4 Drawing Sheets

OTHER PUBLICATIONS

Wang, T., "Synthesis and Properties of N-Acetimidoyl Derivatives of Glycine and Sarcosine", *J. Org. Chem*, 39:3591–3594 (1974).

G.R. Griffiths et al., "Accumulation of Analog of Phosphocreatine in Muscle of Chicks Fed 1-Carboxymethyl-2-iminoimidazolidine (Cyclocreatine)", *J. Biol. Chem.*, 251:2049–2054 (Apr. 1976).

T.M. Annesley et al., "Cyclocreatine Phosphate as a Substitute for Creatine Phosphate in Vertebrate Tissues. Energetic Considerations", *Biochem. Biophys. Res. Commun.*, 74:185–190 (1977).

M.C. Berenbaum, "Synergy, Additivism and Antagonism in Immunosuppression", A Critical Review., *Clin. Exp. Immunol.*, 28:1–18 (1977).

D.F. Deen et al., "Isobologram Analysis of X-Ray-BCNU Interactions In Vitro", *Radiat. Res.*, 79:483–491 (1979).

J.B. Walker, "Creatine: Biosynthesis, Regulation, and Function", *Adv. Enzymol.*, 50:177–241 (1979).

Lowe et al., "Evidence for an Associative Mechanism in the Phosphoryl Transfer Step Catalyzed by Rabbit Muscle Creatine Kinase", *J. Biol. Chem.*, 225:3944–3951 (May 1980).

Summerhayes et al., "Unusual Retention of Rhodamine 123 by Mitochondria in Muscle and Carcinoma Cells", *Proc. Natl. Acad. Sci. USA*, 79: 5292–5296 (Sep. 1982).

Roberts et al., "Synthesis and Accumulation of an Extremely Stable High-Energy Phosphate Compound by Muscle, Heart, and Brain of Animals Fed the Creatine Analog, 1-Carboxyethyl-2-iminoimidazolidine (Homocyclocreatine)" *Arch. Biochem. Biophys.*, 220:563–571 (Feb. 1983).

D.N. Carney et al., "Elevated Serum Creatine Kinase BB Levels in Patients with Small Cell Lung Cancer", *Cancer Res.*, 44:5399–5403 (Nov. 1984).

L.C. Mahadevan et al., "The Brain Isoform of a Key ATP-Regulating Enzyme, Creatine Kinase, is a Phosphoprotein", *Biochem.*, 222:139–144 (1984).

Roberts et al., "Higher Homolog and N-Ethyl Analog of Creatine as Synthetic Phosphagen Precursors in Brain, Heart, and Muscle, Repressors of Liver Amidinotransferase, and Substrates for Creatine Catabolic Enzymes", *J. Biol. Chem.*, 260:13502–13508 (Nov. 1985).

B.A. Teicher et al., "Alkylating Agents: In Vitro Studies of Cross-Resistance Patterns", *Cancer Res.*, 46:4379–4383 (Sep. 1986).

B.A. Teicher et al., "Characterization of a Human Squamous Carcinoma Cell Line Resistant to Cis–Diamminedichloroplatinum(II)", *Cancer Res.*, 47:388–393 (Jan. 1987).

B.A. Teicher et al., "Combination of N,N',N''-Triethylenethiophosphoramide and Cyclophosphamide In Vitro and In Vivo", *Cancer Res.*, 48:94–100 (Jan. 1988).

S. Becker et al., "Investigations on the Function of Creatine Kinase in Ehrlich Ascites Tumor Cells", *Biol. Chem. Hoppe-Seyler*, 370:357–364 (Apr. 1989).

K. Chida et al., "Purification and Identification of Creatine Phosphokinase B as a Substrate of Protein Kinase C in Mouse Skin In Vivo", *Biochem. Biophys. Res. Commun.*, 173:351–357 (Nov. 1990).

A.F.G. Quest et al., "Phosphorylation of Chicken Brain-Type Creatine Kinase Affects a Physiologically Important Kinetic Parameter and Gives Rise to Protein Microheterogeneity In Vivo", *FEBS Lett.*, 269:457–464 (Sep. 1990).

Y. Ohira et al., "Reduced Growth of Ehrlich Ascites Tumor Cells in Creatine Depleted Mice Fed β–Guanidinopropionic Acid", *Biochim. Biophys. Acta*, 1097:117–122 (1991).

B.A. Teicher et al., "Characteristics of Five Human Tumor Cell lines and Sublines Resistant to Cis–Diamminedichloroplatinum(II)", *Int. J. Cancer*, 47:252–260 (1991).

B.A. Teicher et al., "Chemotherapeutic Potentiation Through Interaction at the Level of DNA", In: *Synergism and Antagonism in Chemotherapy*, Academic Press, New York, pp. 541–583, T.C. Chow and D.C. Rideout, Ed. (1991).

T. Walliman et al., "Intracellular Compartmentation, Structure and Function of Creatine Kinase Isoenzymes in Tissues with High and Fluctuating Energy Demands: The 'Phosphocreatine Circuit' for Cellular Energy Homeostasis", *Biochem. J.*, 281:21–40 (1992).

J.W. Lillie et al., "Cyclocreatine (1-Carboxymethyl-2-iminoimidazolidine) Inhibits Growth of a Broad Spectrum of Cancer Cells Derived from Solid Tumors", *Cancer Res.*, 53:3172–3178 (Jul. 1993).

E.E. Miller et al., "Inhibition of Rate of Tumor Growth by Creatine and Cyclocreatine", *Proc. Nat. Acad. Sci. U.S.A.*, 90:3304–3308 (Apr. 1993).

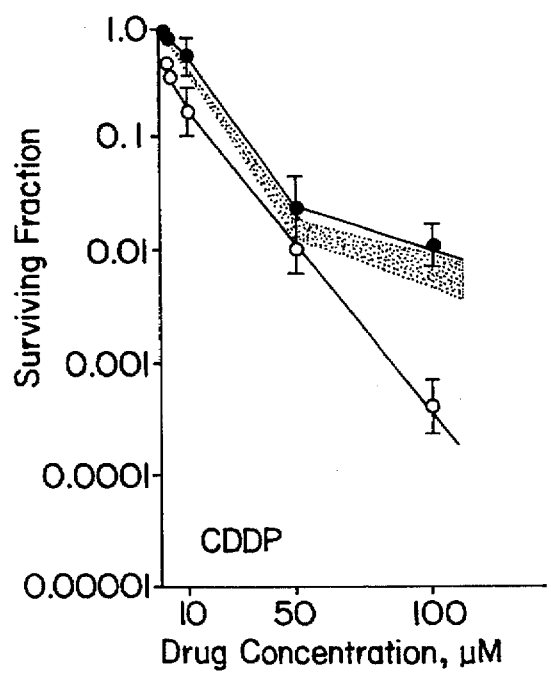
FIG. 2 CDDP
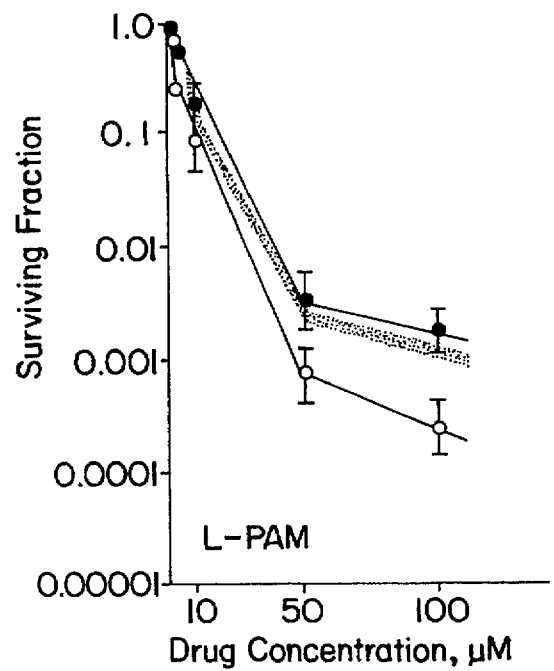
FIG. 3 L-PAM
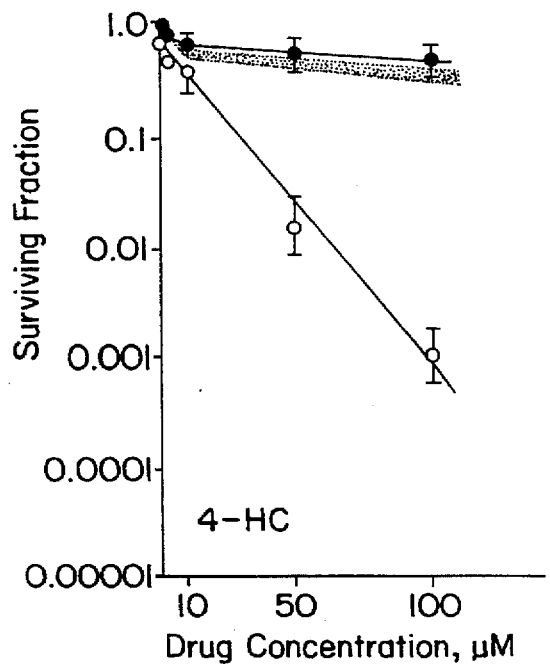
FIG. 4 4-HC
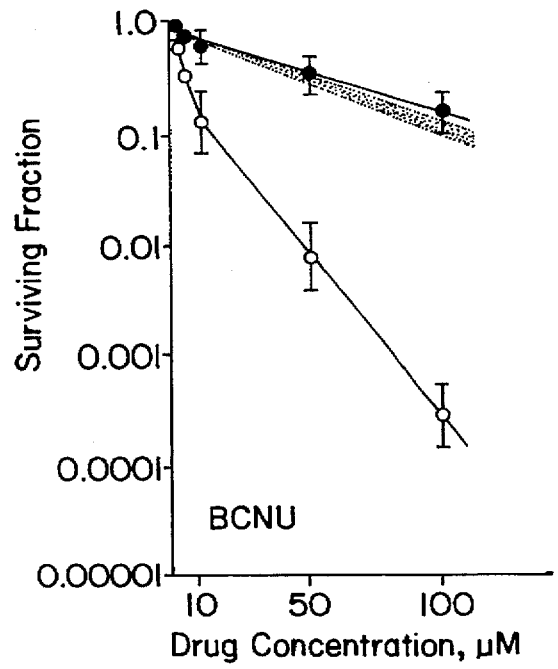
FIG. 5 BCNU

METHODS OF INHIBITING UNDESIRABLE CELL GROWTH USING A COMBINATION OF A CYCLOCREATINE COMPOUND AND A HYPERPLASTIC INHIBITORY AGENT

RELATED APPLICATIONS

This application is a continuation-in-part application of U.S. Ser. No. 07/610,418, now U.S. Pat. No. 5,324,731, filed Nov. 7, 1990, which is a continuation-in-part of U.S. Ser. No. 07/467,147 filed Jan. 18, 1990, now abandoned, which is a continuation-in-part of U.S. Ser. No. 07/344,963 filed Apr. 28, 1989, now abandoned, which is a continuation-in-part of U.S. Ser. No. 07/310,773 filed Feb. 14, 1989, now abandoned. This application also is related to U.S. Ser. No. 07/812,561. This application also contains creatine compounds which overlap with those described in the aforementioned applications. The contents of each of the aforementioned applications are expressly incorporated by reference.

GOVERNMENT SUPPORT

Work related to this invention was supported by NIH grant #RO1-50174.

BACKGROUND OF THE INVENTION

Worldwide, cancer is a leading cause of death. Presently, few cures exist for treating the various types of cancer. Among the possible cures that do exist include the application of tumor-inhibiting compounds (chemotherapy), radiation therapy, and bone-marrow transplants.

Prior art chemotherapy treatments typically include the application of chemotherapeutic agents to a patient in selected dosages to achieve and maintain a therapeutically effective level of the agents in the patient. However, most known chemotherapeutic agents used for the treatment of cancer display significant side effects. Thus, a drawback of typical chemotherapy treatments is that the compounds employed are non-specific in their activity and accumulate to toxic levels, and hence kill rapidly proliferating normal cells, as well as tumor cells.

Creatine (also known as N-(amidino-N-methylglycine, methylglycosyamine or N-methyl-guanidino acetic acid) is a well-known substance (see *The Merck Index* Ninth Edition, No. 2556 (1976)) and its formula is as follows:

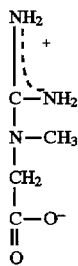

Creatine is present in the muscular tissue, brain and other organs of many vertebrates and the naturally occurring product commercially is extracted from meat. Creatine presently is commercially available and further may be chemically synthesized using conventional techniques such as by heating cyanamide with sarcosine (Strecher *Jahresber. Chem.* (1868), 686; cf. Volhard Z. *Chem.* 5,318 (1869); Paulmann, *Arch. Pharm.* 232, 638 (1894); Bergmann et al. *Z. Physiol. Chem.* 173, 80 (1928); and King J. *Chem. Sec.* (1930), 2374). Creatine analogs are compounds which are stucturally similar to creatine.

SUMMARY OF THE INVENTION

The present invention is based, at least in part, on the discovery that creatine compounds and hyperplastic inhibitory agents, such as chemotherapeutic agents, additively and synergistically combine to inhibit undesirable cell growth, e.g. inappropriate cell growth resulting in undesirable benign conditions or tumor growth. The present invention provides for the use of creatine compounds and hyperplastic inhibitory agents for prophylactic and/or therapeutic treatments of undesirable cell growth. The present invention provides methods of using creatine compounds, in combination with a hyperplastic inhibitory agent, to inhibit the growth of undesirable cell growth in a subject. The combination therapy of the present invention can be advantageous over conventional chemotherapeutic approaches because the synergistic aspect allows the physician to administer less of the hyperplastic inhibitory agent (e.g. chemotherapeutic agent) resulting in less side effects in the patient being treated. The present invention provides a method for inhibiting undesirable cell growth in a subject by administering to a subject an effective mount of a combination of a creatine compound and an effective mount of a hyperplastic inhibitory agent.

The present invention further pertains to compositions for inhibiting undesirable cell growth, e.g. tumor growth, in a subject. The compositions of the present invention include an effective mount of the creatine compound and a hyperplastic inhibitory agent, e.g., a chemotherapeutic agent, in a pharmaceutically acceptable carrier. Other aspects of the invention include packaged creatine compounds and hyperplastic inhibitory agents. The packaged compounds and agents also include instructions for using the creatine compound/inhibitory agent combination for inhibiting undesirable cell growth in a patient or instructions for using the compounds and agents, in selected quantifies, in a pharmaceutically acceptable carrier.

The methods and compositions of the present invention can be used for in vivo therapeutic purposes or can be used ex vivo for purging bone marrow. The bone marrow can be purged with the combination of the creatine compound and the hyperplastic inhibitory agent and then placed back into the same subject or a different subject in its purged form. The methods and compositions of this invention also can be used in ex vivo screening assays for tissue or cells removed during surgery to determine whether the tissue or cells are cancerous or benign.

BRIEF DESCRIPTION OF THE FIGURES

FIGS. 2 is a graph depicting the survival fraction of exponentially growing human small-cell lung carcinoma that are exposed to a creatine compound for 24 hours along with various concentrations of cis-diaminedichloroplatinum (II) (CDDP).

FIGS. 3 is a graph depicting the survival fraction of exponentially growing human small-cell lung carcinoma that are exposed to a creatine compound for 24 hours along with various concentrations of mephalan (L-PAM).

FIGS. 4 is a graph depicting the survival fraction of exponentially growing human small-cell lung carcinoma that are exposed to a creatine compound for 24 hours along with various concentrations of 4-hydroperoxy-cyclophosphamide (4-HC).

FIGS. 5 is a graph depicting the survival fraction of exponentially growing human small-cell lung carcinoma that are exposed to a creatine compound for 24 hours along with various concentrations of carmustine (BCNU).

DETAILED DESCRIPTION

Figure 1:
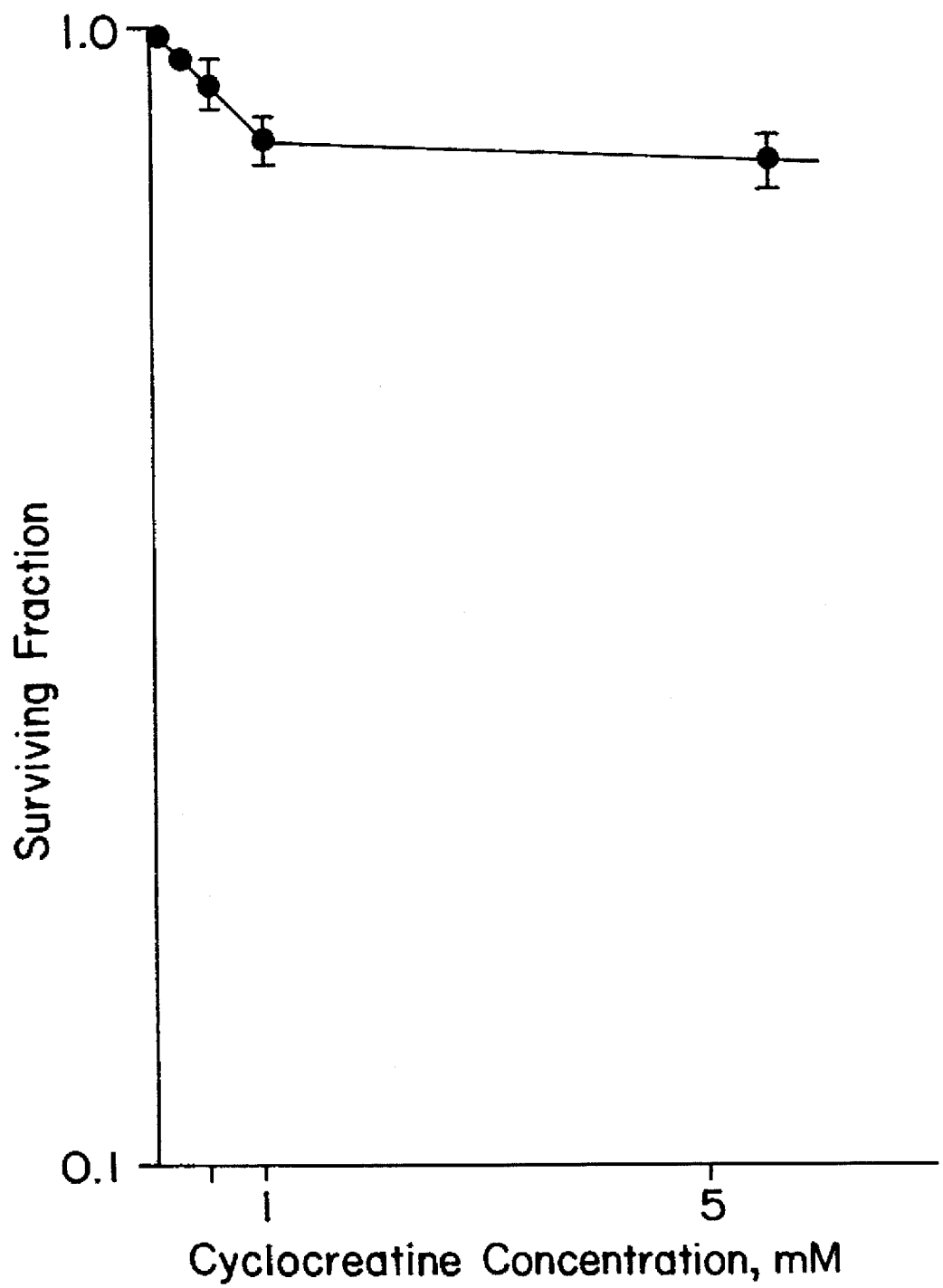
FIG. 1 is a graph depicting the survival fraction of exponentially growing human small-cell lung carcinoma cells that are exposed to various concentrations of a creatine compound for twenty-four hours.

The present invention pertains to a method of inhibiting undesirable cell growth in a subject. The method involves the administration of an effective amount of a creatine compound and a hyperplastic inhibitory agent (hereinafter inhibitory agent) to the subject such that growth of the undesirable cell(s) is inhibited.

The term "administering" is intended to include routes of administration which allow the creatine compound and/or inhibitory agent to perform their intended functions of inhibiting undesirable cell growth. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the creatine compound or inhibitory agent can be coated with or disposed in a selected material to protect it from natural conditions which may detrimentally effect its ability to perform its intended function. The creatine compound can be administered alone, or in conjunction with either an inhibitory agent or with a pharmaceutically acceptable carrier, or both. Further the creatine compound can be administered as a mixture of creatine compounds, which also can be coadministered with at least one inhibitory agent, or pharmaceutically acceptable carrier, or both. The creatine compound can be administered prior to the administration of the inhibitory agent, simultaneously with the inhibitory agent, or after the administration of the inhibitory agent. The creatine compound also can be administered as a prodrug which is converted to its active form in vivo.

The language "pharmaceutically acceptable carrier" is intended to include substances capable of being coadministered with the creatine compound(s) and/or the inhibitory agent(s), and which allows both to perform their intended function of inhibiting undesirable cell growth in a subject. Examples of such carriers include solutions, solvents, dispersion media, delay agents, emulsions and the like. The use of such media for pharmaceutically active substances are well known in the art. Any other conventional carrier suitable for use with the creatine compound and/or with the inhibitory agent(s) also fall within the scope of the present invention.

The language "effective amount" of the combination of the creatine compound and the inhibitory agent is that amount necessary or sufficient to inhibit the undesirable cell growth, e.g. prevent the undesirable cell growth, or reduce the size of a pre-existing benign cell mass or malignant tumor in the subject. The effective amount can vary depending on such factors as the type of cell growth being treated or inhibited, the type of inhibitory agent(s) employed, the particular creatine compound, the size of the subject, or the severity of the undesirable cell growth or rumor. For example, the choice of each of the individual agents (creatine compound or inhibitory agent) which make up the combination can affect what constitutes an "effective amount". One of ordinary skill in the art would be able to study the aforementioned factors and make the determination regarding the effective amount of the combination of the creatine compound and inhibitory agent without undue experimentation. An in vitro assay as described in Example 1 below or an assay similar thereto (e.g., differing in choice of cell line) also can be used to determine an "effective amount" of the combination of creatine compound and inhibitory agent. The ordinarily skilled artisan would select an appropriate amount of each individual agent in the combination for use in the aforementioned in vitro assay. The cell survival fraction can be used to determine whether the selected amounts were an "effective amount" for the particular combination of agents. For example, the selected amounts used within the assay preferably should result in a killing of at least 50% of the cells, more preferably 75%, and most preferably at least 95%.

The regimen of administration also can affect what constitutes an effective amount. The creatine compound can be administered to the subject prior to, simultaneously with, or after the administration of the inhibitory agent(s). Further, several divided dosages, as well as staggered dosages, can be administered daily or sequentially, or the dose can be continuously infused. Further, the dosages of the compound and the agent(s) can be proportionally increased or decreased as indicated by the exigencies of the therapeutic situation.

Creatine, commonly known as N-(amidino N-methylglycine, methylglycosyamine, or N-methylguanidino acetic acid) is a well known substance (see *The Merck Index* Ninth Edition, No. 2556 (1976)) and its formula is as follows:

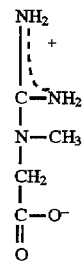

Creatine and phosphorylated creatine are generally present in the muscular tissue, brain and other organs of many vertebrates, and the naturally occurring product that is commercially available is usually extracted from meat. The terms creatine or creatine compound are intended to include both the isolated naturally occurring form, and the chemically synthesized form. Presently, creatine is commercially available and can be chemically synthesized using conventional techniques such as by heating cyanamide with sarcosine (Strecher, *Jahresber. Chem.* 686 (1868)); Paulmann, Arch, Pharm. 232, 638 (1894); and King J., *Chem. Soc.* 2374 (1930)).

The language "creatine compound" is intended to include creatine and compounds which are structurally similar to creatine and/or analogs of creatine. The language "creatine compound" can also include "mimics" or "inhibitors of creatine kinase". "Mimics" is intended to include compounds which may not be structurally similar to creatine but mimic the therapeutic activity of creatine or structurally similar creatine compounds in vivo. The "inhibitors of creatine kinase" are compounds which inhibit the activity of the enzyme. The creatine compounds of this invention are those compounds which are useful for inhibiting tumor growth in subjects (patients). The term creatine compound also is intended to include pharmaceutically acceptable salts of the compounds. Creatine compounds have previously been described in copending application Ser. No. 07/061, 677 entitled Methods of Treating Body Parts Susceptible to Ischemia Using Creatine Analogs, filed May 14, 1993; copending application Ser. No. 08/009,638 entitled Creatine Phosphate, Creatine Phosphate Analogs and Uses Therefor, filed on Jan. 27, 1993; copending application Ser. No. 07/812,561 entitled Creatine Analogs Having Antiviral Activity, filed Dec. 20, 1991; and copending application Ser. No. 07/610,418 entitled Method of Inhibiting transformation of Cells in Which Purine Metabolic Enzyme Activity is Elevated, filed Nov. 7, 1990. The entire contents of each of the copending applications are herein expressly incorporated by reference, along with their published foreign counterparts; and all of the creatine compounds along with their methods of synthesis and selection discussed in the aforementioned applications are intended to be part of this invention unless specifically stated otherwise.

The preferred creatine compounds of this invention are those encompassed by formula (I) set forth below:

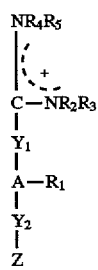
(I)

wherein A is selected from the group consisting of N or CH;

Z is selected from the group consisting of

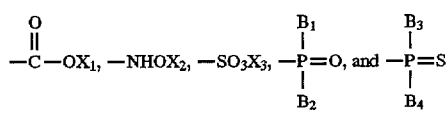

wherein $B_1$–$B_4$ are each independently selected from hydrogen and $OX_4$ and $X_1$–$X_4$ are each independently selected from the group consisting of hydrogen, alkyl, alkenyl, alkynyl and pharmaceutically acceptable salts;

$Y_1$ and $Y_2$ are each independently selected from the group consisting of a direct bond, alkylene, alkenylene, alkynylene and alkoxylene;

$R_1$ is selected from the group consisting of hydrogen, hydroxyl, alkyl, alkenyl, alkynyl, and alkoxyl; and $R_2$–$R_5$, if present, are each independently selected from the group consisting of hydrogen, a phosphorous containing moiety, alkyl, alkenyl, alkynyl, alkoxyl and haloalkyl, wherein A may form a ring structure from with one of the nitrogens in the amidino moiety or with $Y_2$.

A preferred subgenus of the above formula (I) compounds encompassed by formula (II) set forth below, wherein the variables are as defined above in formula (I).

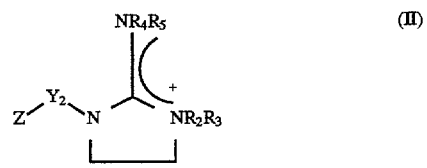
(II)

The alkylene, alkenylene, alkynylene, alkyl, alkenyl and alkynyl groups (hereinafter hydrocarbon groups) may have straight or branched chains. The unsaturated groups may have a single site of unsaturation or a plurality of sites of unsaturation. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynylene, propyl, propylene, propenyl, propenylene, propynyl, and propynylene. Examples of higher hydrocarbon groups (from four to about ten carbons) include butyl, t-butyl, butenyl, butenylene, and butynyl, butynylene, nonyl, nonylene, nonenyl, nonenylene, nonynyl, and nonynylene.

The alkoxy, haloalkyl, alkoxyene, and haloalkylene groups (hereinafter substituted hydrocarbon groups) are alkyl or alkylene groups substituted with one or more oxygen or halogen atoms. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodine. Examples of substituted hydrocarbon groups which are useful within this invention are similar to hydrocarbon groups set forth above except for the incorporation of oxygen(s) or halogen(s) into the groups.

The language "pharmaceutically acceptable salt" (as a possibility for "X" in formula (I) and as it pertains to creatine compound salts) is intended to include pharmaceutically acceptable salts capable of being solvated under physiological conditions. Examples of such salts include sodium, e.g. disodium, potassium, e.g. dipotassium, and hemisulfate. The term is further intended to include lower hydrocarbon groups capable of being solvated under physiological conditions, i.e. alkyl esters, e.g. methyl, ethyl and propyl esters.

For purposes of this invention, the amidino moiety of formula (I) is depicted below:

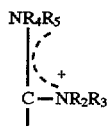

The nitrogens in this moiety can form a ring structure with A. The ring can be a hydrocarbon ring or a hetero ring containing atoms such as O, N or S. The ring structure further can be a single ring or alternatively can be a fused ring system. The preferred ring structures are single rings having five, six or seven ring members and most preferably five membered rings such as those present in cyclocreatine- or carbocreatine-like compounds.

The creatine compounds of this invention preferably possess inherent characteristics enhancing their ability to perform their intended function of inhibiting tumor growth. For example, the creatine compounds preferably have a solubility which allows them to be delivered in vivo and/or are capable of acting as substrates for creatine kinase. Some examples of creatine compounds of the present invention are set forth below in Table 1.

TABLE 1

Prephosphagens

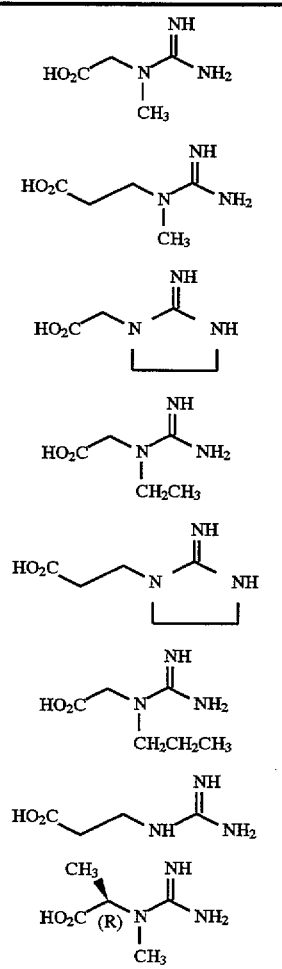

TABLE 1-continued

Prephosphagens

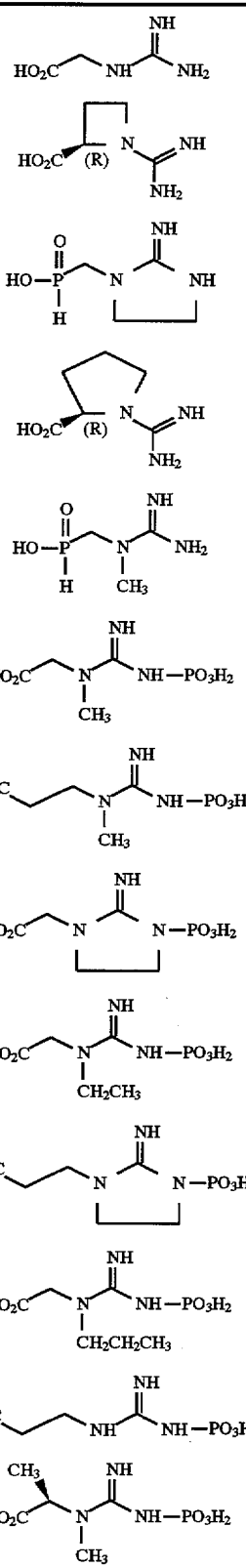

TABLE 1-continued

Prephosphagens

[Chemical structures of prephosphagens:

HO₂C-NH-C(=NH)-NH-PO₃H₂

HO₂C-(R)-[N-C(=NH)-NH-PO₃H₂] (cyclic)

HO-P(=O)(H)-CH₂-N-C(=NH)-N-PO₃H₂ (cyclic)

HO₂C-(R)-[N-C(=NH)-NH-PO₃H₂] (pyrrolidine ring)

HO-P(=O)(H)-CH₂-N(CH₃)-C(=NH)-NH-PO₃H₂]

The creatine compounds can be purchased or alternatively can be synthesized using conventional techniques. For example, creatine can be used as the starting material for synthesizing at least some of the analogs encompassed by formula I. Appropriate synthesis reagents, e.g. alkylating, alkenylating or alkynylating agents can be used to attach the respective groups to target sites, e.g. a nitrogen in the guanidino moiety. Appropriate protecting groups can be employed to prevent reaction at undesired sites in the molecules.

If the creatine compound contains a ring structure, e.g., one of the nitrogens in the amidino moiety forms a rings with "A" or "Y₂", then the analog can be synthesized in a manner analogous to that described for cyclocreatine (Wang, T., *J. Org. Chem.*, 39:3591–3594 (1974)). The various "R", "X" groups can be introduced before or after the ring is formed and "Y" group can be introduced before the ring is formed.

Many creatine compounds have been previously synthesized and described (Rowley et al. *J. Am. Chem.*, 247:5542–5551 (1971); McLaughlin, et all, *J. Biol. Chem.*, 247:4382–4388 (1972); Nguyen, A. C. K., "Synthesis and enzyme studies using creating analogs", Thesis, Dept. of Pharmaceutical Chemistry, Univ. Calif., San Francisco (1983); Lowe et al. *J. Biol. Chem.*, 225:3944–3951 (1980); Roberts et al., *J. Biol, Chem.*, 260: 13502–13508 (1985); Roberts et al., *Arch. Biochem. Biophys.*, 220:563–571 (1983); and Griffiths et al., *J. Biol. Chem.* 251:2049–2054 (1976). The creatine compounds of this invention can be synthesized chemically or enzymatically. The chemical conversion of the prephosphagens (see Table 1) to the respective phosphagens can be done in the same manner as that described by Annesley et al. (*Biol. Chem. Biophys. Res. Commun.* (1977) 74:185–190). Disodium salts of the creatine analogs can be prepared as describe in aforementioned copending application Ser. No. 08/009,638 filed Jan. 27, 1993. The contents of all of the aforementioned references are expressly incorporated by reference. Further to the aforementioned references, Kaddurah-Daouk et al. (WO92/08456) also provide citations for the synthesis of a plurality of creatine analogs (see Examples 2 and 3 including Table 4). The contents of the entire Kaddurah-Daouk et al. published patent application including the contents of any references cited therein also are expressly incorporated by reference.

Some specific examples of creatine compounds of the present invention include cyclocreatine (CCr), CCr phosphate, creatine, creatine phosphate (phosphocreatine), homocyclocreatine and homocyclocreatine phosphate. Cyclocreatine is an essentially planar cyclic analog of creatine. Although cyclocreatine is structurally similar to creatine, the two compounds are distinguishable both kinetically and thermodynamically. Cyclocreatine is phosphorylated efficiently by creatine kinase in the forward reaction both in vitro and in vivo. In the reverse reaction, however, cyclocreatine phosphate (N-phosphorocyclocreatine, P-cyclocreatine) is dephosphorylated relatively slowly.

The phosphorylated compound P-cyclocreatine is structurally similar to phosphocreatine; however, the phosphorous-nitrogen (P-N) bond of cyclocreatine phosphate is more stable than that of phosphocreatine. Creatine compounds which can act as substrates for creatine kinase are at least some of the compounds which are intended to be part of this invention. Examples of such creatine compounds include the phosphagens and prephosphagens, e.g. see Table 1. Specific examples include cyclocreatine (CCr), CCr phosphate, creatine, creatine phosphate (phosphocreatine), homocyclocreatine and homocyclocreatine phosphate.

The term "subject" is intended to include mammals having undesirable cell growth, e.g. tumors, or which are susceptible to undesirable cell growth, e.g. tumors. Examples of such subjects include humans, dogs, cats, pigs, cows, horses, rats, and mice.

The language "hyperplastic inhibitory agent" is intended to include agents that inhibit the growth of proliferating cells or tissue wherein the growth of such cells or tissues is undesirable. For example, the inhibition can be of the growth of malignant cells such as in neoplasms or benign cells such as in tissues where the growth is inappropriate. Examples of the types of agents which can be used include chemotherapeutic agents, radiation therapy treatments and associated radioactive compounds and methods, and immunotoxins.

The language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics*, 8th Ed., Sec 12:1202–1263 (1990)), and are typically used to treat neoplastic diseases. The chemotherapeutic agents generally employed in chemotherapy treatments are listed below in Table 2.

TABLE 2

| CLASS | TYPE OF AGENT | NONPROPRIETARY NAMES (OTHER NAMES) |
|---|---|---|
| Alkylating | Nitrogen Mustards | Mechlorethemine (HN₂) |
|  |  | Cyclophosphamide |
|  |  | Ifosfamide |
|  |  | Melphalan (L-sarcolysin) |
|  |  | Chlorambucil |

TABLE 2-continued

| CLASS | TYPE OF AGENT | NONPROPRIETARY NAMES (OTHER NAMES) |
|---|---|---|
| Alkylating | Ethylenimines and Methylmelamines | Hexamethylmetamine Thiotepa |
|  | Alkyl Sulfonates | Busulfan |
|  | Nitrosoureas | Carmustine (BCNU) Lomustine (CCNU) Semustine (methyl-CCNU) Streptozocin (streptozotocin) |
|  | Triazenes | Decarbazine (DTIC; dimethyltriazenoimi-dazolecarboxamide) |
|  | Alkylator | cis-diamminedichloroplatinum II (CDDP) |
| Antimetabolites | Folic Acid Analogs | Methotrexate (amethopterin) |
|  | Pyrimidine Analogs | Fluorouracil ('5-fluorouracil; 5-FU) Floxuridine (fluorode-oxyuridine; FUdR) Cytarabine (cytosine arabinoside) Mercaptopuine (6-mercaptopurine; 6-MP) |
|  | Purine Analogs and Related Inhibitors | Thioguanine (6-thioguanine; TG) Pentostatin (2'-deoxycoformycin) |
| Natural Products | Vinca Alkaloids | Vinblastin (VLB) Vineristine |
|  | Topoisomerase Inhibitors | Etoposide Teniposide Camptothecin Topotecan 9-amino-campotothecin CPT-11 |
|  | Antibiotics | Dactinomycin (actinomycin D) Adriamycin Daunorubicin (dannomycin; rubindomycin) Dozorubicin Bleomycin Plicamycin (mithramycin) Mitomycin (mitomycin C) Taxol Taxotere |
|  | Enzymes | L-Asparaginase |
|  | Biological Response Modifiers | Interfon alfa interleukin 2 |
| Miscellaneous Agents | Platinum Coordination Complexes | cis-diamminedichloroplatinum II (CDDP) Carboplatin |
|  | Anthracendione | Mitoxantrone |
|  | Substituted Urea | Hydroxyurea |
|  | Methyl Hydraxzine Derivative | Procarbazine (N-methylhydrazine, (MIH) |
|  | Adrenocortical Suppressant | Mitotane (o,p'-DDD) Aminoglutethimide |
| Hormones and Antagonists | Adrenocorticosteroids | Prednisone |
|  | Progestins | Hydroxyprogesterone caproate Medroryprogesterone acetate Megestrol acetate |
|  | Estrogens | Diethylstilbestrol Ethinyl estradiol |
|  | Antiestrogen | Tamoxifen |
|  | Androgens | Testosterone propionate Fluoxymesterone |
|  | Antiandrogen | Flutamide |
|  | Gonadotropin-releasing hormone analog | Leuprolide |

The language "radiation therapy" is intended to include the application of a genetically and somatically safe level of x-rays, both localized and non-localized, to a subject to inhibit, reduce, or prevent symptoms or conditions associated with undesirable cell growth. The term x-rays is intended to include clinically acceptable radioactive elements and isotopes thereof, as well as the radioactive emissions therefrom. Examples of the types of emissions include alpha rays, beta rays including hard betas, high energy electrons, and gamma rays. Radiation therapy is well known in the art (see e.g., Fishbach, F., *Laboratory. Diagnostic Tests*, 3rd Ed., Ch. 10:581–644 (1988)), and is typically used to treat neoplastic diseases.

The term "immunotoxins" includes immunotherapeutic agents which employ cytotoxic T cells and/or antibodies, e.g., monoclonal, polyclonal, phage antibodies, or fragments thereof, which are utilized in the selective destruction of undesirable rapidly proliferating cells. For example, immunotoxins can include antibody-toxin conjugates (e.g., Ab-ricin and Ab-diptheria toxin), antibody-radiolabels (e.g., Ab-$I^{135}$) and antibody activation of the complement at the tumor cell. The use of immunotoxins to inhibit, reduce, or prevent symptoms or conditions associated with neoplastic diseases are well known in the art (see e.g., Harlow, E. and Lane, D., *Antibodies*, (1988)).

The language "inhibiting undesirable cell growth" is intended to include the inhibition of undesirable or inappropriate cell growth. The inhibition is intended to include inhibition of proliferation including rapid proliferation. For example, the cell growth can result in benign masses or the inhibition of cell growth resulting in malignant tumors. Examples of benign conditions which result from inappropriate cell growth or angiogenesis are diabetic retinopathy, retrolental fibrioplasia, neovascular glaucoma, psoriasis, angiofibromas, rheumatoid arthritis, hemangiomas, Karposi's sarcoma, and other conditions or dysfunctions characterized by dysregulated endothelial cell division.

The language "inhibiting tumor growth" is intended to include the prevention of the growth of a tumor in a subject or a reduction in the growth of a pre-existing tumor in a subject. The inhibition also can be the inhibition of the metastasis of a tumor from one site to another. In particular, the language "tumor" is intended to encompass both in vitro and in vivo tumors that form in any organ or body part of the subject. The tumors preferably are tumors sensitive to the creatine compounds of the present invention. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The present invention further pertains to a therapeutic and prophylactic composition for inhibiting tumor growth in a subject. The composition contains an effective amount of a creatine compound, an effective amount of a hyperplastic inhibitory agent, preferably a inhibitory agent, and a pharmaceutically acceptable carrier.

The present invention further pertains to packaged tumor growth inhibitors containing a creatine compound and an inhibitory agent as described above, packaged with instructions for using the creatine compound and inhibitory agent as tumor growth inhibitor(s). The instructions would provide such information as the appropriate dose of creatine and/or inhibitory agent or the appropriate regimen.

The following invention is further illustrated by the following examples, which should not be construed as further limiting. The contents of all references, pending patent applications and published patents, cited throughout this application are hereby expressly incorporated by reference. The animal models used throughout the Examples are accepted animal models and the demonstration of efficacy in these animal models is predictive of efficacy in humans.

EXAMPLES

The following methodology described in the Materials and Methods section was used throughout the in vitro and/or in vivo examples set forth below.

Materials and Methods

Compounds

Cyclocreatine was prepared according to a published protocol (Griffiths G. R. and Walker J. B., *J. Biol. Chem.*, 251: 2049–2054, (1976)). Cis-diamminedichloroplatinum (II) (CDDP), melphalan (L-PAM), cyclophosphamide (CTX), 5-fluorouracil (5-FU), and adriamycin were purchased from Sigma Chemical Co., St. Louis, Mo., U.S.A.; 4-hydroperoxycyclophosphamide (4-HC) was obtained from Asta Medica, Frankfurt am Main, Germany; and Carmustine (BCNU) and Etoposide was obtained from the Dana-Farber Cancer Institute pharmacy, USA.

Cell Lines

The SW2 human small-cell lung carcinoma cell line was initiated from pleural fluid obtained from a patient with small-cell carcinoma (Francis J. et al., *AACR Proceedings*, 21:52 (1980); and Francis K. et al., *Cancer Res.*, 43:639–645 (1983)). These cells were grown exponentially in RPMI 1640 (Gibco, Grand Island, N.Y.) supplemented with 10% fetal bovine serum (FBS) (Sterile Systems, Logan, Utah), and with antibiotics as enlarging spheroids with a doubling time of 2–4 days; eventually reaching a plateau by day 30. The spheroids were dispersed to make a single-cell suspension for drag exposure. The colonies were grown in soft agar, and the plating efficiency of this cell line 10%–15%.

MCF-7 human adenocarcinoma cells of the breast (developed by Dr. M. Rich of the Michigan Cancer Foundation) were also used in this invention. The MCF-7 cell line has been used as a model for in vitro studies of breast carcinoma (Summerhayes et al., *Proc. Natl. Acad. Sci. USA*, 79:5292–5296 (1982)). These cells were grown as monolayers in DME supplemented with antibiotics, L-glutamine, and 10% fetal bovine serum, and had a plating efficiency of 25–40%.

Survival Curves

SW2 cells experiencing exponential growth were exposed to various concentrations of cyclocreatine from 0.5 mM to 5 mM for 24 hours, or were exposed to 0.5 mM of cyclocreatine for 24 hours with exposure to various concentrations of BCNU, CDDP, 4-HC or L-PAM during the fifth hour of cyclocreatine treatment. After exposure to the various inhibitory agents, the cells were first washed three times with phosphate buffered 0.9% saline solution, and then were plated in duplicate at three dilutions on 0.5% soft agar for colony formation, as described above. The overall results were expressed as the surviving fraction of treated cells as compared with vehicle-treated control cells (Teicher B. A. et al., *Cancer Res.*, 46:4379–4383 (1986); Teicher B. A. et al., *Cancer Res.*, 47:388–393 (1987); and Teicher B. A. et al., *Int. J. Cancer*, 47:252–260 (1991)).

All results were expressed as a mean±standard error of the mean, and additivity analysis of the survival curves was performed. Isobolograms (envelopes) were generated for the special case in which the dose of one agent is held constant. Dose-response curves for each agent alone were generated. Combinations of creatine compounds and inhibitory agents producing an effect within the generated isobologram envelope boundaries were considered to be additive. Specifically, those isobolograms displaced to the left of the envelope were greater than additive (i.e., supra-additive), whereas those displaced to the right were less than additive (i.e., infra-additive) (Berenbaum M. C., *Clino Exp. Immunol.*, 28: 1–18 (1977)). This general approach can be extrapolated to the special case in which the level of an agent is held constant. Under these conditions, an isobologram can be derived that plots the expected effect for any level of the variable agent combined with the fixed agent. Experimentally, this approach readily facilitates the determination of additive and nonadditive combinations. To facilitate isobologram analysis, a flexible, interactive computer program was developed. The computer program first deduced the best-fitting dose-response curve(s) using applied dose (or log dose) and effect, log effect probit-percentage effect, or logit-percentage effect relationships. For cell-survival, dose-response curves depicting correlations of greater than or equal to 0.96 were obtained. The program then generated an isobologram at a constant level of the selected agent.

Additionally, MCF-7 cells experiencing exponential growth were exposed to various concentrations of cyclocreatine from 0.5 mM for 24 hours, or were exposed to 0.5 mM of cyclocreatine for 24 hours with exposure to various concentrations of adriamycin, CDDP, etoposide, or taxol during the fifth hour of cyclocreatine treatment. After exposure to the foregoing inhibitory agents, the cells were washed three times with phosphate buffered 0.9% saline solution, and then were plated in duplicate at three dilutions in monolayer for colony formation. The overall results were expressed as the surviving fraction of treated cells as compared with vehicle-treated control cells (Teicher B. A. et al., *Cancer Research*, 47:252–260(1991)).

Data Analysis

Isobologram methodology was used to determine additivity/synergy of the foregoing combination treatments. (See Berenbaum cited supra (1977)).

Tumors

The rat mammary adenocarcinoma 13672 is a carcinogen induced (DMBA) tumor of the female Fischer 344 rat (Segaloff A., *Recent Prog. Hormone Res.*, 22:351–374 (1966)). The tumor can metastasize to the lung and abdominal organs. The tumor is composed of epithelial tissue in folds and acini, where the acini have a high level of mitoses. The acini are preferably double or triple cell layered, and can also be cuboidal, columnar or pseudocolumnar in shape. Preferably, the tumor growth is invasive. The creatine kinase activity in the 13672 tumor was determined to be 0.26 U/mg protein at 37° C. Tumor cells, in the order of $2\times10^6$, were prepared from a brew of stock tumors for implantation subcutaneously in the hind legs of 8 to 10 week old rats on day 0. The tumor grew to a size of about 1 cm$^3$ in about 28 days when implanted s.c. in the hind leg.

The glioblastoma multiforma T98G is a tumor from a human male patient (*J. Cell Physiol.*, 99:43–54 (1979)). The cells grew in monolayer culture or as nodular xenografts in nude mice. The T98G cells were prepared from a brew of stock tumors which were implanted subcutaneously in a hind leg of nude mice.

Tumor Growth Delay

The size of each tumor was measured thrice weekly until it reached a volume of about 500 mm$^3$. Tumor growth delay was calculated as the days taken by each individual tumor to reach 500 mm$^3$ compared with the untreated controls. Each treatment group had 4 animals and the experiment was repeated three times. Days of tumor growth delay are the mean±standard error for the treatment group compared with the control.

Example 1

The In Vitro Tumor Growth Inhibitory Effect of the Combination of a Creatine Compound and a Hyperplastic Inhibitory Agent FIG. 1 is a graph depicting the effect of concentrations of cyclocreatine up to 5 mM for 24 hours on human SW2 small-cell lung carcinoma cells. The surviving fraction was determined as discussed above in the "Material and Method" section. The results are presented as the mean values±SEM for three independent experiments.

FIGS. 2–5 are graphs depicting the effects of the combination therapies (cyclocreatine and chemotherapeutic agent) on human SW2 small-cell lung carcinoma cells expressed in terms of surviving fraction. The survival curves for exponentially growing SW2 cells after 1 hour exposure to each of the four preferred antitumor alkylating agents are shown in FIGS. 2–5. The cyclocreatine/antitumor alkylating agent regimen consisted of a 24 hour exposure of the cells to 0.5 mM cyclocreatine with a 1 hour exposure to an antitumor alkylating agent during the fifth hour so that cyclocreatine was present prior to, during and after application of the antitumor alkylating agent. Solid symbols (●) represent the survival for each of the antitumor alkylating agents alone (1 hour) and shaded areas represent the envelopes of additivity determined by isobologram analysis. The open circle symbols (o) represents the survival for each of the combinations of cyclocreatine and the antitumor alkylating agent. The results are presented as the mean values of±SEM for three independent experiments. The combination of cyclocreatine and CDDP (FIG. 2) resulted in additive-to-greater-than-additive killing of SW2 cells, with the greatest synergy occurring at high concentrations of CDDP. The combination of cyclocreatine and L-PAM (FIG. 3) also produced additive-to-greater-than-additive killing of SW2 cells. The level of synergy with the cyclocreatine/L-PAM combination also increased with increasing L-PAM concentrations.

As shown in FIG. 4, the SW2 cells are relatively resistant to the cytotoxic effects of 4-HC, such that 100 µM of 4-HC for 1 hour only kills about 50% of the cells. The combination of cyclocreatine and 4-HC produced significantly greater-than-additive tumor cell killing so that at 50 µM of 4-HC about 1.5 logs more cells were killed, and at 100 µM of 4-HC at about 2.5 logs again more cells were killed than when compared to the combined cytotoxicity of the agents.

SW2 cells are only moderately sensitive to BCNU. As shown in FIG. 5, one log (or 90%) of SW2 cells were killed by exposure to about 140 µM of BCNU for 1 hour. The combination of cyclocreatine and BCNU resulted in significantly greater-than-additive killing over the BCNU concentration range examined. By way of example, with a concentration of 50 µM of BCNU along with cyclocreatine, there were about 1.5 logs greater killing of SW2 cells than expected for additivity. When 100 µM of BCNU were administered along with cyclocreatine, there were 2.5 logs greater killing of SW2 cells than expected for additivity of the two compounds.

Example 2

The In Vivo Tumor Growth Inhibitory, Effect of the Combination of a Creatine Compound and a Hyperplastic Inhibitory Agent Cyclocreatine inhibits the growth of 13672 rat mammary carcinoma. Cyclocreatine was administered to 13672 tumor bearing Fisher 344 rats by intraperitoneal injection, and preferably by intravenous injection, via the tail vein (see Table 3).

TABLE 3

Growth delay of the rat 13672 mammary carcinoma produced by daily doses of cyclocreatine that was administered intraperitoneally (ip) or intravenously (iv).[a]

| Cyclocreatine Dose, g/kg | Administration Route | Schedule, days | Initial Tumor Volume, mm$^3$ | Tumor Growth Delay[b] days |
|---|---|---|---|---|
| 0.5 | ip | 4–17 | 25 | 3.0 ± 0.4 |
| 0.5 | ip | 11–17 | 100 | 1.8 ± 0.3 |
| 1 | ip | 4–17 | 25 | 4.8 ± 0.6* |
| 1 | ip | 11–17 | 100 | 1.6 ± 0.4 |
| 0.5 | iv | 4–8 | 25 | 4.8 ± 0.6 |
| 0.5 | iv | 7–11 | 50 | 3.3 ± 0.4 |
| 0.5 | iv | 11–15 | 100 | 1.8 ± 0.3 |
| 1 | iv | 4–8 | 25 | 7.6 ± 1.0* |
| 1 | iv | 7–11 | 50 | 3.8 ± 0.6 |
| 1 | iv | 11–15 | 100 | 1.5 ± 0.3 |

[a]Data are presented as the means of 4 animals per group and the experiment was performed three times (n = 12).
[b]Tumor growth delay is the difference in number of days for treated tumors to reach a volume of 500 mm$^3$ compared with untreated controls. Control tumors reach 500 mm$^3$ in 18.0 ± 1.5 days.
*Significantly different from the control group by the Dunn multiple comparisons test; $p < 0.01$.

Several schedules of daily cyclocreatine administration were studied beginning either 4, 7 or 11 days post tumor cell implantation, thus allowing treatment of tumors of various volumes (various tumor cell burdens). Cyclocreatine, administered at either 0.5 g/kg or 1 g/kg, produced measurable growth delay of the 13672 tumor. For example, cyclocreatine was more effective at the 1 g/kg dose than when administered at the 0.5 g/kg dose. The drug was also more effective when administered as an intravenous injection than as an intraperitoneal injection, when beginning at the same tumor volume, even though the intravenous schedule was 5 daily injections compared with 14 daily injections for the intraperitoneal schedule (Table 3). As would be expected for most antitumor treatments, cyclocreatine at the 1 g/kg dose was most effective when the tumor burden (tumor volume) was smaller, producing a maximal tumor growth delay of 7.6 days when administered intravenously, daily for 5 days, beginning on day 4 post-tumor cell implantation.

When treatment with cyclocreatine at the 0.5 g/kg or 1 g/kg doses, and administered intravenously, was extended to two 5-day courses with a 5-day interval therebetween, an increase in tumor growth delay was observed when compared with a single 5-day course of the drag (see Table 4). The effect of the cyclocreatine dose was significant in that two course at a dose of 0.5 g/kg was less effective than a single course at 1 g/kg when treatment was initiated on day 4.

TABLE 4

Growth delay of the rat 13672 mammary carcinoma produced by cyclocreatine that is administered intravenously.[a]

| Initial Tumor Cyclocreatine Dose, g/kg | Schedule, days | Tumor Volume, $mm^3$ | Growth Delay[b] days |
|---|---|---|---|
| 0.5 | 4–8 | 25 | 4.8 ± 0.6 |
| 0.5 | 7–11 | 50 | 3.3 ± 0.4 |
| 1 | 4–8 | 25 | 7.6 ± 1.0 |
| 1 | 7–11 | 50 | 3.8 ± 0.6 |
| 0.5 | 4–8; 14–18 | 25 | 6.4 ± 1.0* |
| 0.5 | 7–11; 14–18 | 50 | 6.7 ± 1.1* |
| 1 | 4–8; 14–18 | 25 | 10.1 ± 1.2** |
| 1 | 7–11; 14–18 | 50 | 8.3 ± 1.2** |

[a]Data are presented as the means of two experiments with 4 animals per group, therefore n = 8.
[b]Tumor growth delay is the difference in number of days for treated tumors to reach a volume of 500 $mm^3$ compared with untreated controls. Control tumors reach 500 $mm^3$ in 18.0 ± 1.5 days.
*Significantly different from the control group by the Dunn multiple comparisons test; $P < 0.01$; **$p < 0.001$.

For initial combination treatments employing cyclocreatine and inhibitory agents, cyclocreatine at a 1 g/kg dose was administered beginning two (2) days before the standard agents, and continued daily over the course of those therapies for a total of 7 injections, as shown in Table 5 below. Each of the standard inhibitory agents were administered by way of intraperitoneal injection, at a standard dosage and on a standard schedule, for the particular agent. For example, CDDP (8 mg/kg) was administered as a single dose on day 7 and produced a tumor growth delay of about 7 days, which was increased to about 11 days when combined with cyclocreatine. Adriamycin (1.75 mg/kg) when administered daily for 5 days on days 7–11 produced a tumor growth delay of about 5 days, which increased to about 6.5 days when combined with cyclocreatine. Further, cyclophosphamide (100 mg/kg) was administered on alternate days for 3 injections beginning on days 7, 9 and 11, and produced about 9 days of tumor growth delay in the 13672 tumor. This delay was increased to about 11 days when administered in combination with cyclocreatine. In addition, 5-fluorouracil (30 mg/kg) was administered daily for 5 days from days 7–11, resulting in 5.5 days of tumor growth delay when administered alone. When combined with cyclocreatine there was a tumor growth delay of about 7.7 days.

TABLE 5

Growth delay of the rat 13672 mammary carcinoma produced by chemotherapeutic agents in the presence or absence of cyclocreatine that is administered intravenously.[a]

| Treatment Group | Compound Alone | Tumor Growth Delay, Days[b] (Compound + CCr)[c] | |
|---|---|---|---|
| | | 2 days prior | 3 days prior to Compound |
| Cyclocreatine (CCr) (1 g/kg) d5-d11 | | 2.6 ± 4 | 4.1 ± 0.5 |
| CDDP (8 mg/kg) d7 | 7.2 ± 0.6 | 1.0 ± 1.1 | 14.0 ± 1.2** |
| adriamycin (1.75 mg/kg) d7-11 | 5.3 ± 0.5 | 6.5 ± 0.7 | 12.5 ± 1.1** |
| cyclophosphamide (100 mg/kg) d7, 9, 11 | 9.3 ± 0.7 | 10.7 ± 1.0 | 16.2 ± 1.3** |
| 5-fluorouracil (30 mg/kg) d7-11 | 5.5 ± 0.5 | 7.7 ± 0.9 | 11.8 ± 1.0** |

[a]Data are presented as the means of 2 experiments with 4 animals per group and the experiment was done twice, therefore n = 8.
[b]Tumor growth delay is the difference in number of days for treated tumors to reach a volume of 500 $mm^3$ compared with untreated controls. Control tumors reach 500 $mm^3$ in 18.0 ± 1.5 days.
[c]Cyclocreatine (1 g/kg) was administered intravenously on days 5 through 11 or days 4 through 13 post-tumor cell implantation. All other drugs were administered intraperitoneally on the schedules shown.
*Significantly different from the compound alone group by the Dunn multiple comparisons test; $p < 0.01$; **$p < 0.001$.

In an alternate combination therapy study, treatment with cyclocreatine (1 g/kg) was initiated three (3) days prior to the application of the standard inhibitory agents, and continued through day 13 post tumor cell implantation. This 10-day treatment cycle with cyclocreatine produced an overall tumor growth delay of about 4 days in animals bearing the 13762 mammary carcinoma (see column 4 of Table 5). The 1 0-day cyclocreatine cycle, in combination with the administration of the inhibitory agents, also produced a delay in tumor growth when compared with the 7-day treatment cycle. As further illustrated by Table 5, the 10-day cyclocreatine cycle plus CDDP resulted in a 2-fold increase in tumor growth delay compared with CDDP alone; a 2.4-fold increase in tumor growth delay compared with adriamycin alone; a 1.7-fold increase in tumor growth delay compared with cyclophosphamide alone; and a 2-fold increase in tumor growth delay compared with 5-fluorouracil alone.

As the foregoing illustrates, cyclocreatine and one or more of the inhibitory agents are an effective antitumor combination. Additionally, cyclocreatine in combination with each of the currently used inhibitory agents resulted in longer rumor growth delays than those achieved with any of the inhibitory agents alone. With each standard inhibitory agent, the longer course of 10 days of cyclocreatine administration was a more effective addition to the therapeutic regimen than was the shorter course of 7 days of cyclocreatine administration.

Example 3

Figure 6:
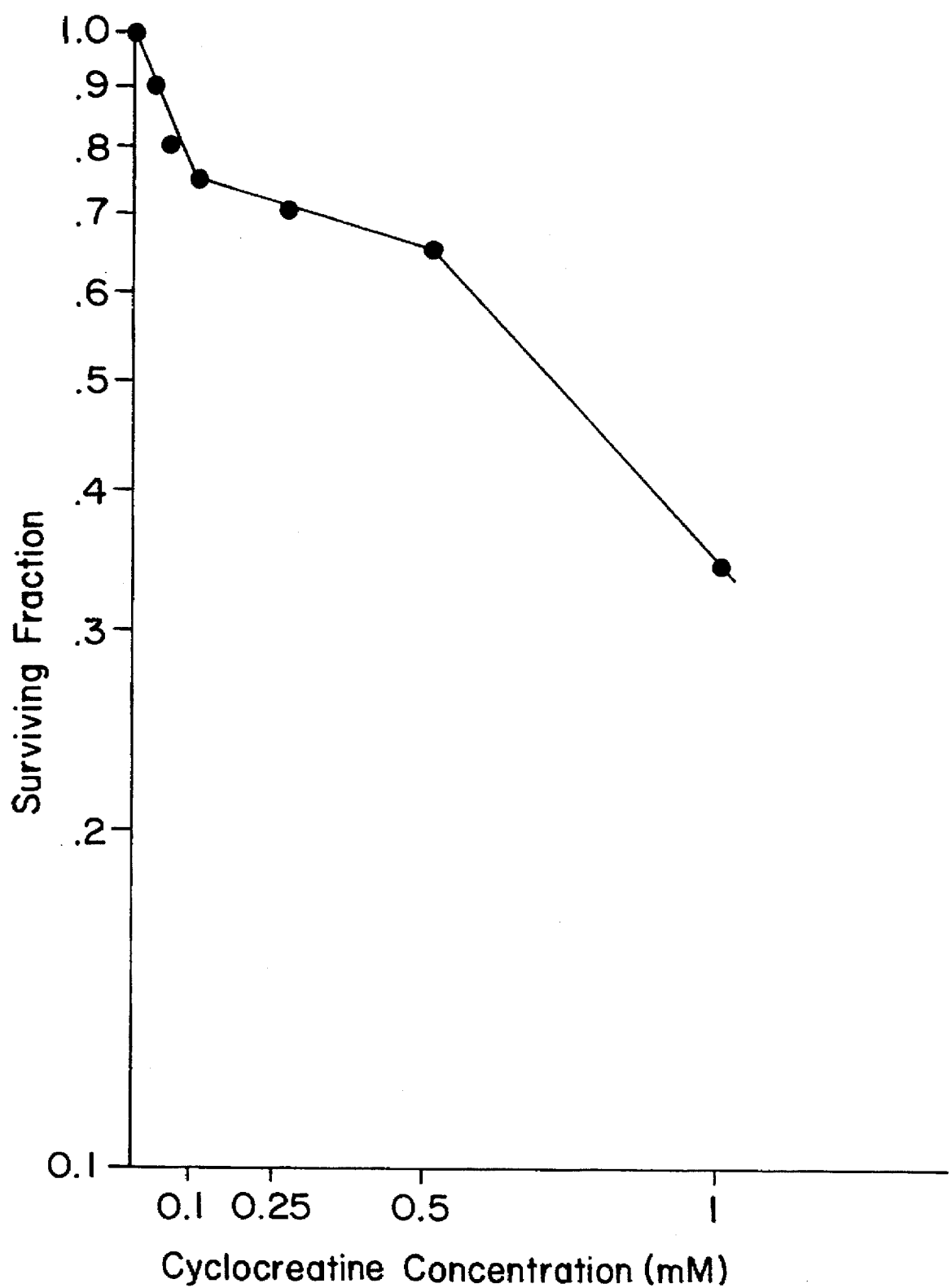
FIG. 6 is a graph depicting the survival fraction of growing human breast adenocarcinoma cells (MCF-7) that are exposed to various concentrations of a creatine compound for twenty-four hours.
Figure 8:
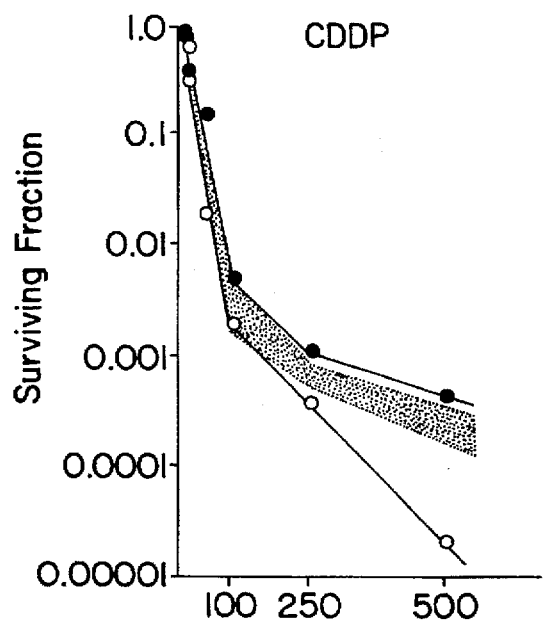
FIG. 8 is a graph depicting the survival fraction of exponentially growing human breast carcinoma cells that are exposed to a creatine compound for 24 hours along with various concentrations of cis-diaminedichloroplatinum (II) (CDDP).
Figure 9:
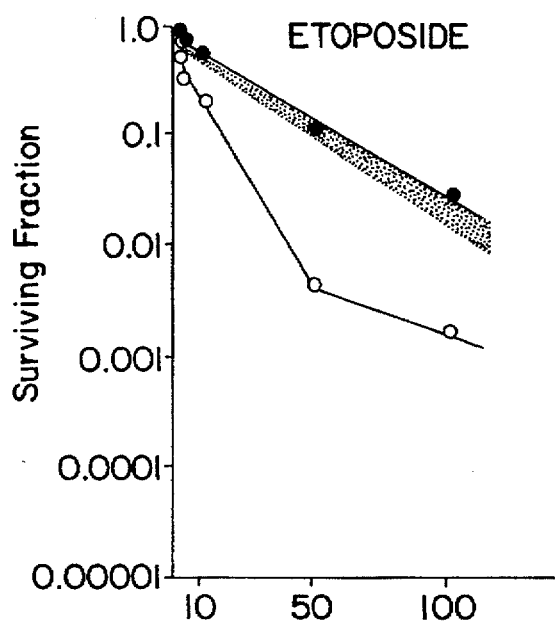
FIG. 9 is a graph depicting the survival fraction of exponentially growing human breast carcinoma cells that are exposed to a creatine compound for 24 hours along with various concentrations of etoposide (etoposide).
Figure 7:
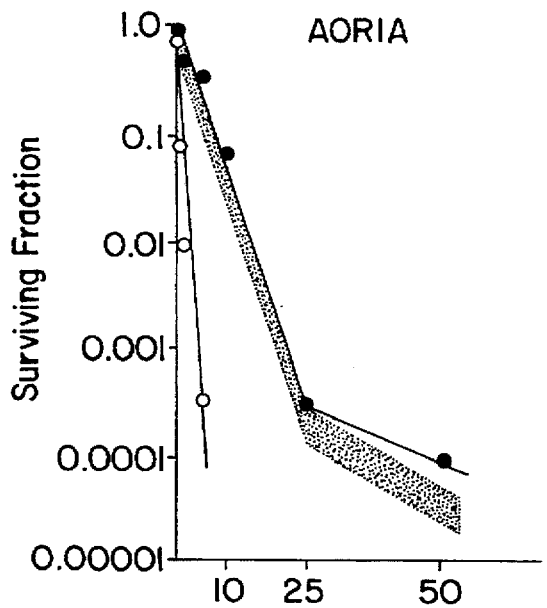
FIG. 7 is a graph depicting the survival fraction of exponentially growing human breast carcinoma cells that are exposed to a creatine compound for 24 hours along with various concentrations of adriamycin (ADRIA).
Figure 10:
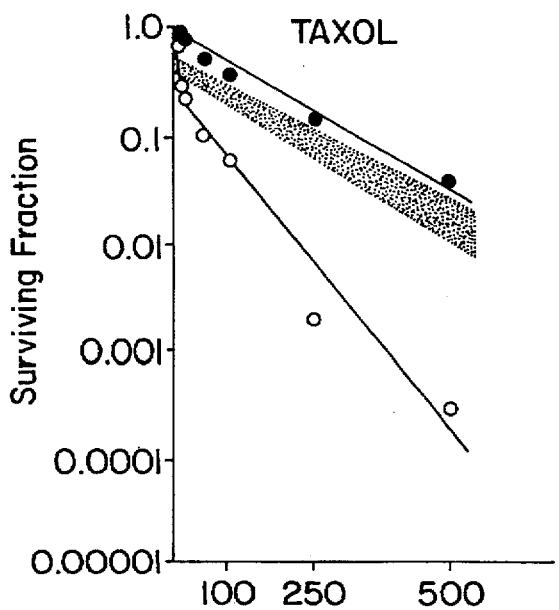
FIG. 10 is a graph depicting the survival fraction of exponentially growing human breast carcinoma cells that are exposed to a creatine compound for 24 hours along with various concentrations of taxol (taxol).

The In Vitro Tumor Cell Growth Inhibitory Effect of the Combination of a Creatine Compound and a Inhibitory agent FIG. 6 illustrates the surviving fraction of growing human breast adenocarcinoma cells (MCF-7) that are exposed to various concentrations of cyclocreatine for twenty-four hours. An exposure concentration of 0.1 mM killed 25% of the exposed MCF-7 cells, while an exposure concentration of 0.5 mM killed 35% of the cells. A cyclocreatine concentration of 0.7 mM killed 50% of the cells.

As shown in FIGS. 7–10, the combination regimens employing cyclocreatine (0.5 mM, 24 hours) and a inhibitory agent, such as CDDP, resulted in additive to greater than additive cytotoxicity toward MCF-7 cells, as shown by the survival fraction of SW2 cells in FIGS. 7–10. The combination of cyclocreatine (0.5 mM, 24 hours) and etoposide, adriamycin or taxol resulted in markedly greater-than-additive killing of MCF-7 cells (see FIGS. 7–10). By way of example, a concentration of 50 µM of etoposide produces about 1 log greater-than-additive cytotoxicity when combined with cyclocreatine. A 5 µM concentration of adriamycin produced about 3 logs greater-than-additive cytotoxicity in MCF-7 cells when combined with cyclocreatine, as compared to the use of adriamycin alone. Finally, at a concentration of 100 µM of taxol there was about 1.5 logs greater-than-additive killing of MCF-7 when cyclocreatine was combined with taxol in the treatment regimen.

Example 4

The In Vivo Tumor Growth Inhibitory Effect of the Combination of a Creatine Compound and a Inhibitory Agent The human T98G glioblastoma (brain tumor cell line) was grown as a xenograft in nude mice. Cyclocreatine, preferably at a concentration of 1 g/kg, was administered intravenously daily beginning on day 4 through day 11 post tumor cell implantation, and then from day 14 through day 18, for a total dose of 13 g/kg. This treatment cycle produced a tumor growth delay of about 3 days in the T98G minor (see Table 6).

TABLE 6

Growth Delay of the Human T98G Glioblastoma Xenograft produced by Anticancer Agents ± Cyclocreatine

| Treatment Group | Tumor Growth Delay Days Compound Alone | Compound + Cyclo (1 g/kg × 13) |
|---|---|---|
| Cyclocreatine (CCr) (1 g/kg) d4-11 and 14–18 | — | 3.0 |
| CDDP (10 mg/kg) d7 | 9.9 | 21.2 |
| Cyclophosphamide d7, d9, d11 (3 × 150 mg/kg) | 7.5 | 15.6 |
| BCNU (3 × 15 mg/kg) d7, d9, d11 | 4.7 | 11.0 |
| Adriamycin (5 × 1.75 mg/kg) d7-17 | 8.6 | 14.9 |

*n = 4 per group
**Cyclocreatine (1 g/kg) days 4–11; 14–18, iv
All other drugs were administered intraperitoneally.

Daily cyclocreatine was administered beginning on days 4 through 11 and on days 14 through 18 post tumor cell implantation. The inhibitory agent CDDP (10 mg/kg) administered as a single dose on day 7 produced a growth delay of about 10 days in the tumor, and the delay was increased to about 21 days when used in combination with cyclocreatine. The tumor, when treated with cyclophosphamide, preferably 150 mg/kg, on days 7, 9 and 11 post tumor cell implantation, experienced a growth delay of about 7.5 days, which increased to about 15 days when used in combination with cyclocreatine. Similarly, when the inhibitory agent BCNU, preferably 15 mg/kg, was administered on days 7, 9 and 11 post cell implantation, the tumor experienced a growth delay of 4.7 days, which increased to 11 days when used in combination with cyclocreatine. Likewise, administering adriamycin, preferably 1.75 mg/kg, on days 7 through 11 produced 8.6 days of tumor growth delay, which increased to about 15 days when used in combination with cyclocreatine.

As the results listed in Table 6 illustrate, the treatment regimen employing combinations of a inhibitory agent and cyclocreatine resulted in longer tumor growth delays than those achieved when the inhibitory agent was used alone. For example, the combination treatments produced about a 2-fold or greater growth delay in the tumor.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A method for inhibiting tumor growth in a mammalian subject, comprising
   administering to a mammalian subject an effective amount of a combination of cyclocreatine and a hyperplastic inhibitory agent such that tumor growth is inhibited.

2. The method of claim 1 wherein tumor growth is inhibited by preventing the occurrence of the tumor.

3. The method of claim 1 wherein tumor growth is inhibited by reducing the growth of a pre-existing tumor.

4. The method of claim 1 wherein the hyperplastic inhibitory agent is an inhibitory agent, radiation therapy treatment or an immunotoxin.

5. The method of claim 1 wherein the hyperplastic inhibitory agent is radiation therapy treatment.

6. The method of claim 1 wherein the hyperplastic inhibitory agent is an immunotoxin.

7. The method of claim 1 further comprising the administration of at least one additional inhibitory agent or creatine compound.

8. The method of claim 1 wherein the cyclocreatine compound is cyclocreatine phosphate.

9. The method of claim 1 wherein the cyclocreatine compound is cyclocreatine.

10. The method of claim 1 wherein the cyclocreatine compound is homocyclocreatine.

11. The method of claim 1 wherein the cyclocreatine compound is homocyclocreatine phosphate.

12. The method of claim 1 wherein the hyperplastic inhibitory agent is cis-diammine dichloroplatinum (II).

13. The method of claim 1 wherein the hyperplastic inhibitory agent is an alkylating agent.

14. The method of claim 13 wherein the alkylating agent is a nitrogen mustard, ethylenimines, methylmelamine, alkyl sulfonate, nitrosourea, or triazene.

15. The method of claim 13 wherein the alkylating agent is melphalan, cyclophosphamide, adriamycin, or carmustine.

16. The method of claim 1 wherein the hyperplastic inhibitory agent is an anti-metabolite.

17. The method of claim 16 wherein the anti-metabolite is a folic acid compound, pyrimidine, or a purine compound.

18. The method of claim 1 wherein the hyperplastic inhibitory agent is a vinca alkaloid, epipodophyllotoxin, antibiotic, enzyme, or a biological response modifier.

19. The method of claim 1 wherein the hyperplastic inhibitory agent is a vinca alkaloid.

20. The method of claim 1 wherein the hyperplastic inhibitory agent is an epipodophyllotoxin.

21. The method of claim 1 wherein the hyperplastic inhibitory agent is an antibiotic.

22. The method of claim 1 wherein the hyperplastic inhibitory agent is an enzyme.

23. The method of claim 1 wherein the hyperplastic inhibitory agent is a biological response modifier.

24. The method of claim 1 wherein the hyperplastic inhibitory agent is a platinum coordination complex, anthracenedione, substituted urea, methyl hydrazine derivative, or an adrenocortical suppressant.

25. The method of claim 1 wherein the hyperplastic inhibitory agent is platinum coordination complexes.

26. The method of claim 1 wherein the hyperplastic inhibitory agent is anthracenedione.

27. The method of claim 1 wherein the hyperplastic inhibitory agent is substituted urea.

28. The method of claim 1 wherein the hyperplastic inhibitory agent is methyl hydrazine derivatives.

29. The method of claim 1 wherein the hyperplastic inhibitory agent is adrenocortical suppressants.

30. The method according to claim 1 wherein the hyperplastic inhibitory agent is a hormone or antagonist.

31. The method of claim 1 wherein the hyperplastic inhibitory agent is a topoisonerase inhibitor.

32. The method of claim 1 wherein the hyperplastic inhibitory agent is taxol.

33. The method according to claim 1 wherein the hyperplastic inhibitory agent is an adrenocorticosteroid, progestin, estrogen, antiestrogen, androgen, antiandrogen, or gonadotropin-releasing hormone.

34. The method of claim 1 wherein the cyclocreatine compound is administered prior to the application of the inhibitory agent.

35. The method of claim 1 wherein the cyclocreatine compound is administered substantially simultaneously with the inhibitory agent.

36. The method of claim 1 wherein the cyclocreatine compound is administered after the hyperplastic inhibitory agent.

37. The method of claim 1 wherein said cyclocreatine compound is administered intravenously.

38. The method of claim 37 wherein the chemotherapuetic agent is administered intraperitoneally.

39. The method of claim 37 wherein the hyperplastic inhibitory agent is administered orally.

40. The method of claim 37 wherein the chemotherapeutic agent is administered intraperitoneally.

41. The method of claim 1 wherein the cyclocreatine compound is cyclocreatine and the hyperplastic inhibitory agent is 4-hydroperoxy cyclophosphamide, cis-diamminedichloroplatinum (II), adriamycin, cyclophosphamide, 5-fluorouracil, melphalan; etoposide or carmustine.

42. The method of claim 1 wherein the cyclocreatine compound is cyclocreatine and the hyperplastic inhibitory agent is 4-hydroperoxycyclophosphamide.

43. The method of claim 1 wherein the cyclocreatine compound is cyclocreatine and the hyperplastic inhibitory agent is cis-diamminedichloroplatinum (II).

44. The method of claim 1 wherein the cyclocreatine compound is cyclocreatine and the hyperplastic inhibitory agent is melphalan.

45. The method of claim 1 wherein the cyclocreatine compound is cyclocreatine and the hyperplastic inhibitory agent is carmustine.

46. The method of claim 45 wherein the alkylating agent is adriamycin, cyclophosphamide, 4-hydroperoxycyclophosphamide, or carmustine.

47. The method of claim 1 wherein the cyclocreatine compound is cyclocreatine and the hyperplastic inhibitory agent is adriamycin.

48. The method of claim 1 wherein the cyclocreatine compound is cyclocreatine and the hyperplastic inhibitory agent is cyclophosphamide.

49. The method of claim 1 wherein the cyclocreatine compound is cyclocreatine and the hyperplastic inhibitory agent is 5-fluorouracil.

50. The method of claim 1 wherein the cyclocreatine compound is cyclocreatine and the hyperplastic inhibitory agent is etoposide.

51. The method of claim 1 wherein the cyclocreatine compound is cyclocreatine and the hyperplastic inhibitory agent is an alkylating agent.

52. A composition for inhibiting tumor growth in a mammalian subject, comprising
a synergistically effective mount of a combination of a cyclocreatine
compound and an immunotoxin, and
a pharmaceutically acceptable carrier.

53. A composition for inhibiting tumor growth in a mammalian subject, comprising
a synergistically effective amount of a combination of a cyclocreatine compound and a hyperplastic inhibitory agent, and
a pharmaceutically acceptable carrier.

54. The composition of claim 53 wherein the cyclocreatine compound is cyclocreatine phosphate.

55. The composition of claim 53 wherein the cyclocreatine compound is homocyclocreatine phosphate.

56. The composition of claim 53 wherein the cyclocreatine compound is cyclocreatine.

57. The composition of claim 53 wherein the cyclocreatine compound is homocyclocreatine.

58. The composition of claim 53 wherein the hyperplastic inhibitory agent is an alkylating agent.

59. The composition of claim 58 wherein the alkylating agent is a nitrogen mustard, ethylenimine, methylmelamine, alkyl sulfonate, nitrosourea, or a triazene.

60. The composition of claim 53 wherein the hyperplastic inhibitory agent is an anti-metabolite.

61. The composition of claim 60 wherein the anti-metabolite is a folic acid compound, pyrimidine, or a purine compound.

62. The composition of claim 53 wherein the hyperplastic inhibitory agent is a vinca alkaloid, epipodophllotoxin, antibiotic, enzyme, or a biological response modifier.

63. The composition of claim 53 wherein the hyperplastic inhibitory agent is a platinum coordination complex, anthracendione, urea, methyl hydraxzine derivative, or an adrenocortical suppressant.

64. The composition of claim 53 wherein the hyperplastic inhibitory agent is a hormone or antagonist.

65. The composition of claim 53 wherein the hyperplastic inhibitory agent is an adrenocorticosteroids, protestins, estrogens, antiestrogen, androgens, antiandrogen, or a gonadotropin-releasing hormone.

* * * * *